(12) United States Patent
Nakada (10) Patent No.: US 9,073,092 B2
(45) Date of Patent: Jul. 7, 2015

(54) SHEET REINSPECTION APPARATUS, SHEET INSPECTION SYSTEM, AND SHEET INSPECTION METHOD

(71) Applicant: Kabushiki Kaisha Toshiba, Tokyo (JP)

(72) Inventor: Masashi Nakada, Kawasaki (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 14/025,974

(22) Filed: Sep. 13, 2013

(65) Prior Publication Data

US 2014/0083915 A1 Mar. 27, 2014

(30) Foreign Application Priority Data

Sep. 21, 2012 (JP) .................................. 2012-207766

(51) Int. Cl.
| | |
|---|---|
| *B07C 5/00* | (2006.01) |
| *B07C 5/342* | (2006.01) |
| *B41F 33/00* | (2006.01) |
| *B41F 33/02* | (2006.01) |
| *G07D 11/00* | (2006.01) |
| *G01N 21/89* | (2006.01) |

(52) U.S. Cl.
CPC .............. *B07C 5/342* (2013.01); *B41F 33/0036* (2013.01); *B41F 33/025* (2013.01); *G07D 11/0084* (2013.01); *G01N 2021/8917* (2013.01); *G07D 11/0021* (2013.01)

(58) Field of Classification Search
CPC ... B07C 5/342; B41F 33/0036; B41F 33/025; G07D 11/0084; G07D 11/0021; G01N 2021/8917

USPC ................................ 209/534, 552, 554; 101/2
See application file for complete search history.

(56) References Cited

U.S. PATENT DOCUMENTS

| 5,012,932 A | * | 5/1991 | Omura et al. .................. 209/534 |
| 7,611,045 B1 | | 11/2009 | Lute et al. |
| 2005/0006458 A1 | | 1/2005 | Wanibe et al. |

FOREIGN PATENT DOCUMENTS

| CN | 101295416 A | 10/2008 |
| CN | 102081819 A | 6/2011 |
| CN | 102157024 A | 8/2011 |
| DE | 102006015828 A1 | 10/2007 |
| EP | 2410496 A1 | 1/2012 |

(Continued)

OTHER PUBLICATIONS

Extended European Search Report issued in related European Patent Application No. 13184136.3, mailed on Jan. 7, 2014, 6 pages.

(Continued)

*Primary Examiner* — David H Bollinger
(74) *Attorney, Agent, or Firm* — Baker Botts L.L.P.

(57) ABSTRACT

According to one embodiment, a reinspection apparatus which reinspects rejected sheets rejected from sheet processing apparatus configured to convey sheets at first speed, to inspect conveyed sheet in accordance with first determination threshold, and to reject sheets in accordance with an inspection result, reinspection apparatus includes, conveying unit configured to convey taken sheets at second speed lower than first speed, inspection unit configured to inspect sheets conveyed at second speed, determination unit configured to determine whether to reject sheets, and counting unit configured to count sheets which have been determined not to be rejected.

5 Claims, 7 Drawing Sheets

(56) References Cited

FOREIGN PATENT DOCUMENTS

| EP | 2484523 | A1 | 8/2012 |
|---|---|---|---|
| GB | 2403840 | A | 1/2005 |
| JP | 2007-241742 | A | 9/2007 |
| WO | 2010/110630 | A2 | 9/2010 |

OTHER PUBLICATIONS

Office Action issued in related Chinese Patent Application No. 201310428739.8 mailed Apr. 3, 2015, 34 pages (with translation).

* cited by examiner

SHEET REINSPECTION APPARATUS, SHEET INSPECTION SYSTEM, AND SHEET INSPECTION METHOD

CROSS-REFERENCE TO RELATED APPLICATIONS

This application is based upon and claims the benefit of priority from Japanese Patent Application No. 2012-207766, filed Sep. 21, 2012, the entire contents of which are incorporated herein by reference.

FIELD

Embodiments described herein relate generally to a sheet reinspection apparatus, a sheet inspection system, and a sheet inspection method.

BACKGROUND

Heretofore, for example, a sheet processing apparatus which counts and determines sheets has been in practical use. The sheet processing apparatus takes in one by one sheets input to an input portion, and conveys the sheets to a sheet inspection apparatus. The inspection apparatus performs various kinds of processing of the sheet and determines the state of the sheet.

In accordance with the inspection result by the inspection apparatus, the sheet processing apparatus determines the category of the sheet, the fitness level of the sheet, and the authentication of the sheet. The sheet processing apparatus sorts and accumulates the sheets in accordance with the determination result.

A reinspection apparatus which reinspects sheets (rejected sheets) that cannot be processed by the sheet processing apparatus has also been in practical use. The reinspection apparatus inspects the rejected sheet, and determines the category, fitness level, and authentication of the sheet.

An operator who operates the sheet processing apparatus and the reinspection apparatus inputs, to the reinspection apparatus, the rejected sheet rejected from the sheet processing apparatus. The reinspection apparatus reinspects the input rejected sheet. Higher efficiency of such sheet reinspection is required.

DETAILED DESCRIPTION

In general, according to one embodiment, a reinspection apparatus which reinspects rejected sheets rejected from a sheet processing apparatus configured to convey sheets at a first speed, to inspect the conveyed sheet in accordance with a first determination threshold, and to reject the sheets in accordance with an inspection result, the reinspection apparatus comprises, a taking unit configured to take in, one by one, the sheets as the rejected sheets rejected from the sheet processing apparatus, a conveying unit configured to convey the taken sheets at a second speed lower than the first speed, an inspection unit configured to inspect the sheets conveyed at the second speed, a determination unit configured to determine whether to reject the sheets in accordance with the result of the inspection, a counting unit configured to count the sheets which have been determined not to be rejected in accordance with the result of the determination, and an output unit configured to output the result of the counting.

Hereinafter, embodiments of a sheet reinspection apparatus, a sheet inspection system, and a sheet inspection method will be described in detail with reference to the drawings.

Figure 1:
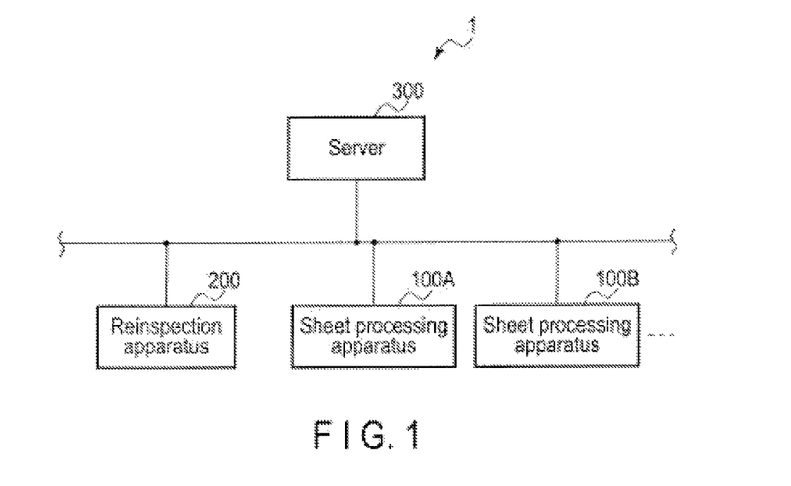
FIG. 1 is an exemplary view for explaining a sheet inspection system according to an embodiment.

FIG. 1 shows an example of the configuration of a sheet inspection system 1 according to one embodiment.

The sheet inspection system 1 comprises at least one or more sheet processing apparatuses 100, a reinspection apparatus 200, and a server 300. The sheet processing apparatuses 100, the reinspection apparatus 200, and the server 300 are connected to one another via a network so that data can be sent and received therebetween.

The sheet processing apparatus 100 takes in a plurality of input sheets one by one at a high speed, and inspects each of the taken sheets for its category, fitness level, and authentication. The sheet processing apparatus 100 counts the sheets judged to be reusable. The sheet processing apparatus 100 binds and discharges the inspected reusable sheets.

The sheet processing apparatus 100 judges whether each of the sheets requires a reinspection. The sheet processing apparatus 100 discharges, as rejected sheets, the sheets judged to require a reinspection.

The sheet processing apparatus 100 processes a batch card inserted in the bundle of sheets. Unique identification information (ID) is printed on the batch card. The sheet processing apparatus 100 optically scans the batch card, and retrieves the identification information.

The sheet processing apparatus 100 associates the counting result of the sheets, the classification of the sheets, the identification information on the batch card, and the determination result with each bundle of sheets. The sheet processing apparatus 100 sends the associated inspection result (including the batch card ID, the classification of the sheets, the number of the sheets, and the determination result) to the server 300.

The sheet processing apparatus 100 discharges the batch card as a rejected sheet. That is, the sheet processing apparatus 100 discharges a bundle including the sheets judged to require a reinspection and the batch card as rejected sheets.

The server 300 stores, in its storage, the inspection result sent from the sheet processing apparatus 100 after attaching an index thereto.

An operator who operates the sheet processing apparatus 100 and the reinspection apparatus 200 inputs, to the reinspection apparatus 200, the rejected sheets discharged (rejected) from the sheet processing apparatus 100. The reinspection apparatus 200 reinspects the input rejected sheets. In this case, the reinspection apparatus 200 processes the bundle including the sheets and the batch card in the same manner as the sheet processing apparatus 100.

The sheet processing apparatus 100 is different from the reinspection apparatus 200 in the required speed of sheet processing. Therefore, the reinspection apparatus 200 conveys the sheets at a lower speed than the sheet processing apparatus 100. The reinspection apparatus 200 can scan the sheets with a higher resolution than the sheet processing apparatus 100. The reinspection apparatus 200 can retrieve the identification information from the batch card inserted between the sheets.

The reinspection apparatus 200 conducts a reinspection in a normal processing mode in a normal state (default state). When operating in the normal processing mode, the reinspection apparatus 200 can inspect sheets with higher accuracy than the sheet processing apparatus 100.

For example, as described above, the reinspection apparatus 200 conveys the sheets at a lower speed than the sheet processing apparatus 100, and can therefore inhibit the flapping of the sheets. Moreover, as described above, the reinspection apparatus 200 scans the sheets at a higher resolution than the sheet processing apparatus 100, and can therefore use finer printing of the sheets for determination. As a result, the reinspection apparatus 200 can make various determinations with higher accuracy.

The reinspection apparatus 200 can conduct a reinspection in a check processing mode. When operating in the check processing mode, the reinspection apparatus 200 can inspect sheets with items fewer than items used to determine the sheets than in the normal processing mode. Thus, when operating in the check processing mode, the reinspection apparatus 200 can exclude, from inspection items, items which can be visually checked by the operator.

Furthermore, the reinspection apparatus 200 may be configured to make various determinations using a threshold different from a threshold in the normal mode when operating in the check processing mode. Thus, the reinspection apparatus 200 can use such a threshold that the sheets are more easily determined to be recirculatable fit sheets. As a result, the reinspection apparatus 200 can prevent the increase of the number of sheet reinspections.

Moreover, the reinspection apparatus 200 can process the sheets in a no-inspection counting mode. When operating in the no-inspection counting mode, the reinspection apparatus 200 counts the number of the sheets without determining the category, authentication, and fitness level of the sheets. That is, the reinspection apparatus 200 can count the number of the sheets which have been visually ascertained to be fit sheets by the operator without determination. As a result, the reinspection apparatus 200 can prevent the increase of the number of sheet reinspections. When operating in the no-inspection counting mode, the reinspection apparatus 200 can cut the counted sheets.

When operating in the no-inspection counting mode, the reinspection apparatus 200 retrieves an image from the sheets. The reinspection apparatus 200 also retrieve a detection value obtained by each inspection unit. When operating in the no-inspection counting mode, the reinspection apparatus 200 stores the images of the sheets, the detection value by each inspection unit, the date of processing, the operator's name, the classification of the sheets, the identification information on the batch card, and other information in association with one another.

The reinspection apparatus 200 associates the counting result of the sheets, the classification of the sheets, the identification information on the batch card, and the determination result with each bundle of the sheets which are rejected sheets. The reinspection apparatus 200 sends the associated reinspection result (including the batch card ID, the classification of the sheets, the number of the sheets, and the determination result) to the server 300.

The server 300 combines the reinspection result sent from the reinspection apparatus 200 with the inspection result sent from the sheet processing apparatus 100, and stores the combined inspection result in a storage medium in the server 300. For example, the server 300 adds the reinspection result to the inspection result which includes identification information corresponding to the identification information included in the reinspection result.

Figure 2:
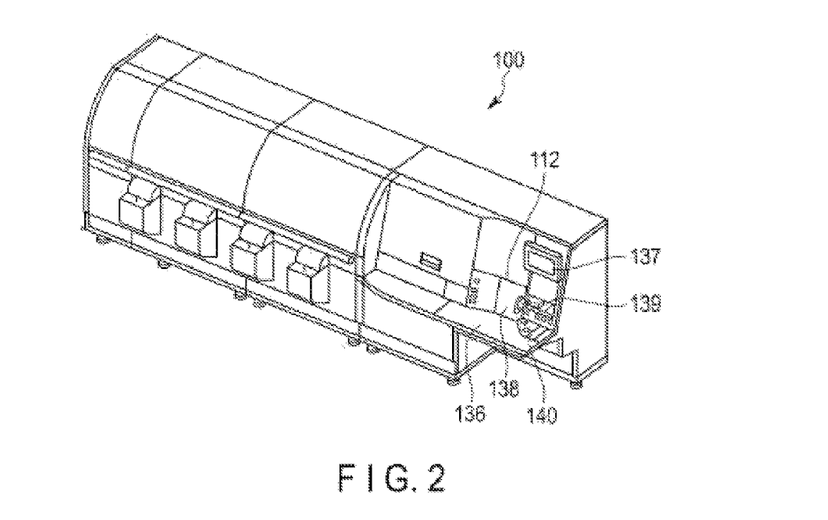
FIG. 2 is an exemplary view for explaining a sheet processing apparatus according to an embodiment.

FIG. 2 shows the appearance of the sheet processing apparatus 100 according to one embodiment.

As shown in FIG. 2, the sheet processing apparatus 100 externally comprises an input portion 112, an operation portion 136, an operation display 137, a door 138, an eject port 139, and a keyboard 140.

The input portion 112 is a component to input a sheet P such as paper money. The input portion 112 collectively receives a stack of sheets P. As described above, a batch card having unique identification information is inserted in the bundle of the sheets P.

The operation portion 136 receives various operation inputs by the operator. The operation display 137 displays various operation guides and processing results to the operator. The operation display 137 may be configured as a touch panel. In this case, the sheet processing apparatus 100 detects the various operation inputs from buttons displayed on the operation display 137 and from the operation of the operation display 137 by the operator.

The door 138 is a door for opening and closing an input port of the input portion 112. The eject port 139 is a component to take out the sheets P from an accumulator in which the sheets P judged to be unrecirculatable by the sheet processing apparatus 100 are stacked. The keyboard 140 functions as an input portion to receive various operation inputs by the operator.

Figure 3:
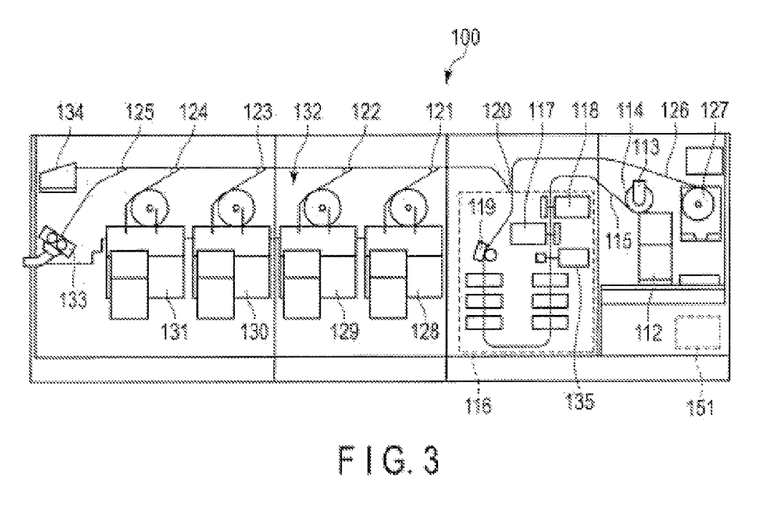
FIG. 3 is an exemplary view for explaining the sheet processing apparatus according to the embodiment.

FIG. 3 shows a configuration example of the sheet processing apparatus 100 in FIG. 2.

The sheet processing apparatus 100 internally comprises the input portion 112, an ejector 113, a suction roller 114, a conveyance path 115, an inspection unit 116, gates 120 to 125, a rejection conveyance path 126, a rejecter/accumulator 127, accumulators/binders 128 to 131, a cutter 133, and a stacker 134. The sheet processing apparatus 100 also comprises a main controller 151. The main controller 151 integrally controls the operations of the components of the sheet processing apparatus 100.

The ejector 113 is provided above the input portion. The ejector 113 comprises the suction roller 114. The suction roller 114 is provided so that the sheets P set in the input portion 112 contact an upper end of an accumulation direction. That is, the suction roller 114 rotates and thereby takes in the sheets P set in the input portion 112 one by one into the apparatus from the upper end of the accumulation direction. For example, the suction roller 114 functions to take out one sheet P for one rotation. The suction roller 114 thereby takes out the sheet P with a constant pitch. The sheet P taken in by the suction roller 114 is introduced into the conveyance path 115. The suction roller 114 may be configured to comprise a suction rotor which uses, for example, suction force generated by a suction pump to suck the surface of the sheet and take out the sheet.

The conveyance path 115 conveys the sheet P to each component in the sheet processing apparatus 100. The conveyance path 115 comprises a conveyer belt and a driving pulley that are not shown. The conveyance path 115 operates the conveyer belt by an unshown driving motor and the driving pulley. The conveyance path 115 uses the conveyer belt to convey the sheet P taken in by the suction roller 114 at a regular speed. The side of the conveyance path 115 close to the ejector 113 is described as an upstream side, and the side close to the stacker 134 is described as a downstream side.

The inspection unit 116 is provided on the conveyance path 115 extending from the ejector 113. The inspection unit 116 comprises an image reader 117, an image reader 118, and a thickness inspection unit 119. The inspection unit 116 detects optical characteristic information, mechanical characteristics, and magnetic characteristic information regarding the sheet P. The sheet processing apparatus 100 thereby detects the kind (category), fitness level, and authentication of the sheet P.

The image readers 117 and 118 are provided to face each other across the conveyance path 115. The image readers 117 and 118 read images on both sides of the sheet P conveyed on the conveyance path 115. Each of the image readers 117 and 118 comprises a charge coupled device (CCD) camera. The sheet processing apparatus 100 retrieves design images on the front and rear sides of the sheet P in accordance with the images obtained by the image readers 117 and 118. The image readers 117 and 118 also retrieve an image of the identification information printed on the batch card, and send the retrieved image to the main controller 151.

The image readers 117 and 118 temporarily store the read images in an unshown memory in the inspection unit 116. The sheet processing apparatus 100 can display the images stored in the memory on the operation display 137 in response to an operation input.

The thickness inspection unit 119 inspects the sheet P conveyed on the conveyance path 115 for its thickness. For example, when the detected thickness is equal to or more than a prescribed value, the sheet processing apparatus 100 detects the doubly taking of sheets P.

The inspection unit 116 also comprises an unshown magnetic sensor. The magnetic sensor detects the magnetic characteristic information regarding the sheet P.

The main controller 151 makes various determinations in accordance with the detection results by the image readers 117 and 118, the thickness inspection unit 119, and the magnetic sensor. For example, the main controller 151 determines the category of the sheet P.

The main controller 151 also determines the authentication of the sheet P. That is, the main controller 151 determines whether the sheet P is genuine or counterfeit.

The main controller 151 also detects the fitness of the sheet P. That is, the main controller 151 determines whether the sheet P is a recirculatable fit sheet or an unrecirculatable unfit sheet.

Furthermore, the main controller 151 determines whether the sheet P is a rejected sheet. That is, the main controller 151 determines, as a rejected sheet, the sheet P which has been determined to be counterfeit, or the sheet P which has been detected to be lying on another sheet by the thickness inspection unit 119, or the sheet P which cannot be identified. The main controller 151 determines, as rejected sheets, the sheets P which have caused a short pitch that leads to incorrect detection by each detector because the distance between the front sheet P and the rear sheet P on the conveyance path is short.

The main controller 151 can recognize the identification information on the batch card in accordance with the image of the identification information on the batch card retrieved by the image readers 117 and 118.

The sheet processing apparatus 100 conveys, to the accumulators/binders 128 to 131, the sheets P which have been determined to be fit sheets. The sheet processing apparatus 100 conveys, to the cutter 133, the sheets P which have been determined to be unfit sheets. The cutter 133 cuts the conveyed unfit sheets. The sheet processing apparatus 100 may convey the unfit sheets to the stacker 134 and accumulate the sheets. For example, the stacker 134 seals, every one hundred accumulated unfit sheets that have arrived.

The sheet processing apparatus 100 conveys, to the rejecter/accumulator 127, the sheets P which have been determined to be rejected sheets. For example, the rejected sheets include doubly-taken sheets that have been abnormally conveyed, defective sheets that are folded or torn, and unidentifiable sheets such as unapproved or counterfeit sheets. The sheet processing apparatus 100 also conveys, to the rejecter/accumulator 127, the sheets P and the batch card inserted between the sheets P as rejected sheets.

The gates 120 to 125 are provided in order on the conveyance path 115 on the downstream side of the inspection unit 116. Each of the gates 120 to 125 is controlled by the main controller 151. The main controller 151 controls the operation of each of the gates 120 to 125 in accordance with the result of the inspection by the inspection unit 116. Thus, the main controller 151 controls so that the sheet P conveyed on the conveyance path 115 will be conveyed to a predetermined processor.

The gate 120 provided immediately after the inspection unit 116 branches the conveyance path 115 to the rejection conveyance path 126. That is, the gate 120 can be switched so that the rejected sheets which have been determined to be genuine as a result of the inspection by the inspection unit 116 or uninspectable sheets which cannot be inspected by the inspection unit 116 are conveyed to the rejection conveyance path 126.

The rejecter/accumulator (rejecter) 127 is provided at the terminal of the rejection conveyance path 126. The rejecter/accumulator 127 accumulates the aforementioned rejected sheets and uninspectable sheets that remain taken out of the ejector 113. The sheets P accumulated in the rejecter/accumulator 127 can be taken out of the eject port 139.

The accumulators/binders 128 to 131 (collectively referred to as an accumulator/binder 132) are provided to branch from the gates 121 to 124, respectively. The sheets P which have been determined to be recirculatable are accumulated in the accumulator/binder 132 according to the category and the front and rear sides. The accumulator/binder 132 binds and stores every predetermined number of accumulated sheets P.

The cutter 133 is provided to branch from the gate 125. The cutter 133 cuts and stores the sheet P. The sheet P conveyed to the gate 125 is a proper sheet P and is a sheet P (unfit sheet) which has been determined to be unrecirculatable.

The stacker 134 is provided at another end of the conveyance path to also branch from the gate 125. When an unfit sheet cutting mode is selected, the main controller 151 controls the gate 125 so that the sheets P are conveyed to the cutter 133. When the unfit sheet cutting mode is not selected, the main controller 151 controls the gate 125 so that the sheets P are conveyed to the stacker 134.

The operator can operate the operation portion 136, the operation display 137, and the keyboard 140 to set any kind (category) of sheet P to be processed by the sheet processing apparatus 100.

The main controller 151 stores, as inspection results, the result of the counting of the sheets P conveyed to the accumulator/binder 132 or the cutter 133, the classification of the sheets, the identification information on the batch card, and the determination result in association with each bundle of the sheets. The main controller 151 also sends the inspection results to the server 300.

Figure 4:
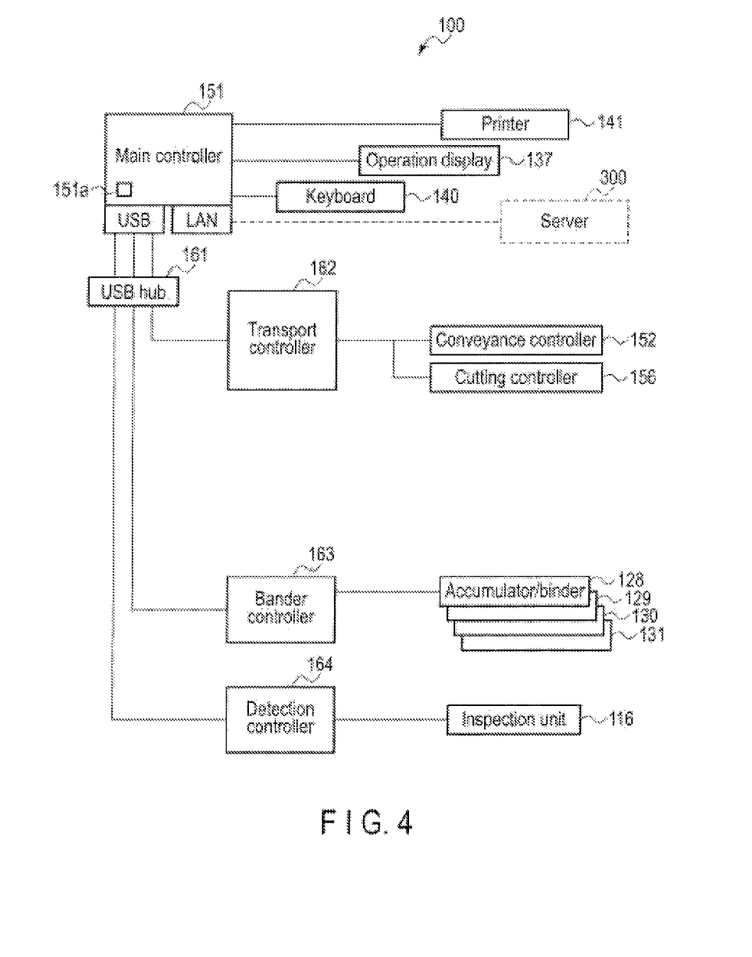
FIG. 4 is an exemplary view for explaining the sheet processing apparatus according to the embodiment.

FIG. 4 shows a configuration example of a control system of the sheet processing apparatus 100 in FIG. 2 and FIG. 3.

The sheet processing apparatus 100 comprises the main controller 151, the inspection unit 116, a conveyance controller 152, a cutting controller 156, the operation display 137, and the keyboard 140. The sheet processing apparatus 100 also comprises a printer 141, a USB hub 161, a transport controller 162, a bander controller 163, and a detection controller 164.

The main controller 151 has overall control of the sheet processing apparatus 100. The main controller 151 can be obtained by, for example, a part of a personal computer (PC). The main controller 151 controls the conveyance controller 152 and the cutting controller 156 in accordance with the operation input by the operation display 137 and the inspection result by the inspection unit 116. The main controller 151 can output processing results as a record by the printer 141.

The USB hub 161 is connected to the main controller 151. The transport controller 162, the bander controller 163, and the detection controller 164 are connected to the USB hub 161.

The main controller 151 can control the operations of the conveyance controller 152, the cutting controller 156, and the ejector 113 via the transport controller 162.

The main controller 151 can also control the operations of the accumulators/binders 128 to 131 via the bander controller 163. The main controller 151 can also control the operation of each detecting device of the inspection unit 116 via the detection controller 164.

For example, the operator uses the operation display 137 or the keyboard 140 to input a threshold for each of the processing items in various determinations regarding the sheet P to be processed, the name of a supplier of the sheet P, and a processing method.

As described above, the inspection unit 116 comprises the image readers 117 and 118, and the thickness inspection unit 119.

The conveyance controller 152 controls the ejector 113, the conveyance path 115, the rejection conveyance path 126, and the gates 120 to 125 under the control of the main controller 151. The conveyance controller 152 thereby controls the taking and conveyance of the sheet P. The conveyance controller 152 also sorts the determined sheets P according to the category. That is, the conveyance controller 152 functions as a sort processor.

For example, the conveyance controller 152 controls the gates 120 to 125 so that the sheet P which has been determined to be an unfit sheet is conveyed to the cutter 133 and the stacker 134. The conveyance controller 152 also controls the gates 120 to 125 so that the sheet P which has been determined to be a rejected sheet and the batch card to the rejecter/accumulator 127.

The bander controller 163 controls the rejecter/accumulator 127 and the accumulators/binders 128 to 131 under the control of the main controller 151. The bander controller 163 thereby controls the accumulation and binding of the sheets P.

The cutting controller 156 controls the operation of the cutter 133 under the control of the main controller 151. The cutter 133 thereby cuts the conveyed sheets P.

The main controller 151 comprises a memory 151a for previously storing a threshold (first determination threshold) for each item of the inspection by each inspector of the inspection unit 116. The main controller 151 compares a detection value detected by each inspector of the inspection unit 116 with the threshold stored in the memory 151a, and determines by the comparison result the category, authentication, and fitness of the sheet P and also determines whether the sheet P is a rejected sheet.

The first determination threshold stored in the memory 151a may be changed in accordance with the input on the operation portion 136, the operation display 137, and the keyboard 140.

Figure 5:
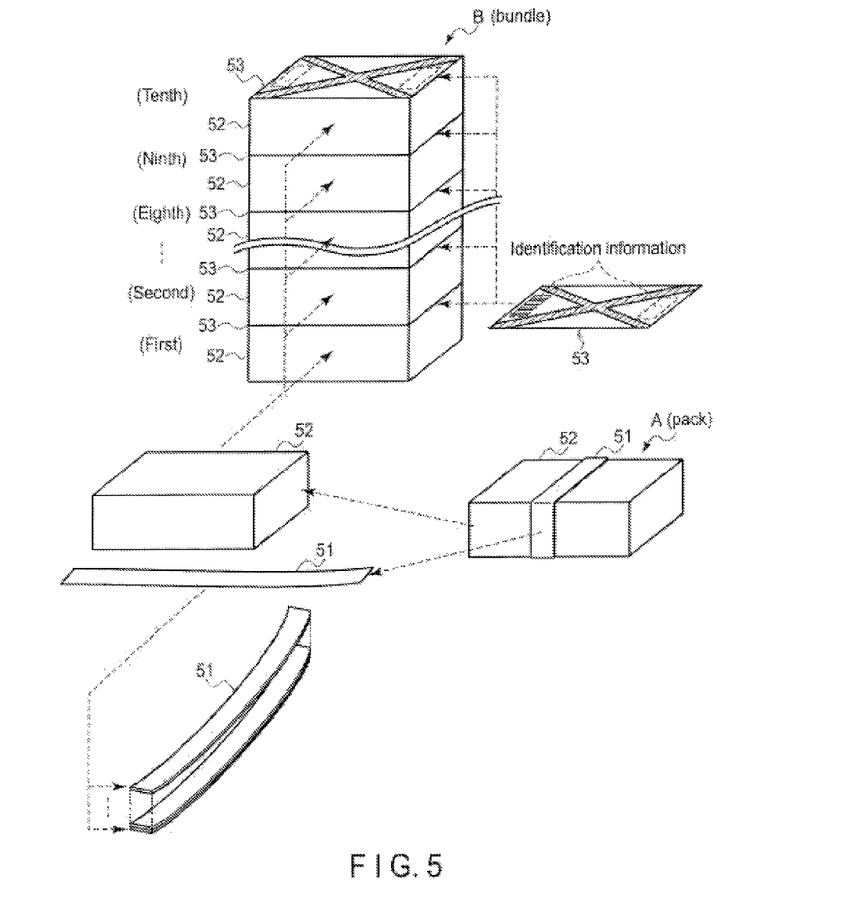
FIG. 5 is an exemplary view for explaining the sheet inspection system according to the embodiment.

FIG. 5 shows an example of a bundle including the sheets P and the batch card to be input to the sheet processing apparatus 100.

First, a bundle B of 1000 sheets P is made. There are two ways of making the bundle B as follows.

The first way is to stack ten packs 52 of 100 sheets P from which sealing strips 51 collected by the same collecting facility are removed. In this case, one batch card 53 is inserted into the bundle B of 1000 sheets P.

The second way is to insert the batch card 53 into every bundle 52 of sheets P without a sealing strip collected by a different collecting facility.

The batch card 53 is inserted into the bundle 52 of sheets P by the operator before the processing by the sheet processing apparatus 100.

Figure 6:
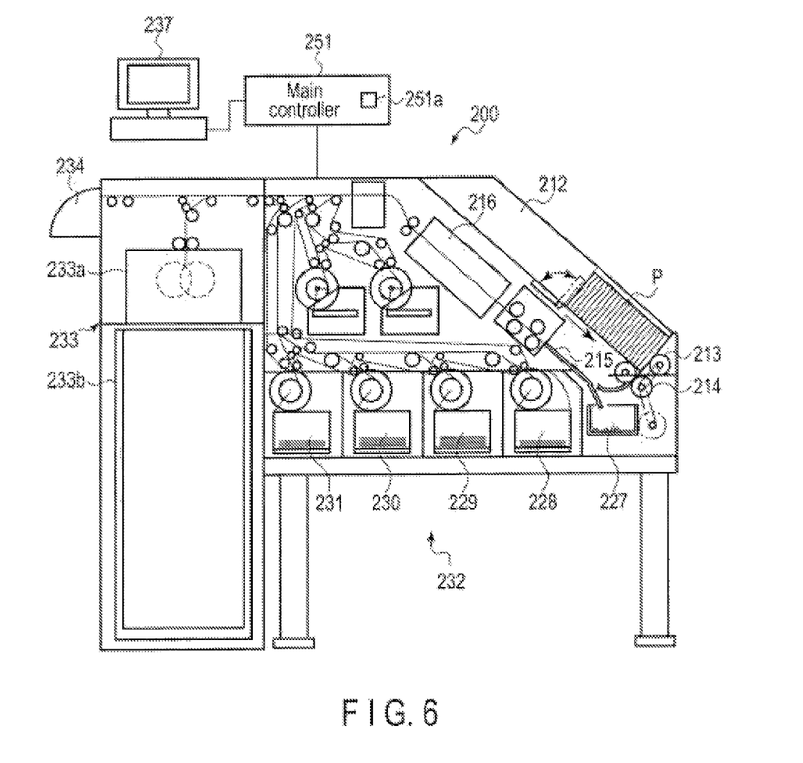
FIG. 6 is an exemplary view for explaining a sheet reinspection apparatus according to the embodiment.

FIG. 6 shows an example of the configuration of the reinspection apparatus 200.

The operator takes out the rejected sheets discharged from the sheet processing apparatus 100, and supplies the rejected sheets to the input portion of the reinspection apparatus 200. The rejected sheets are discharged from the sheet processing apparatus 100 so that the discharged sheets P and the batch card are stacked.

The reinspection apparatus 200 externally comprises an input portion 212 and an operation display 237. The reinspection apparatus 200 also internally comprises an ejector 213, a suction roller 214, a conveyance path 215, an inspection unit 216, accumulators 228 to 231, a cutter 233, and a rejecter/accumulator 234. The reinspection apparatus 200 also comprises a main controller 251. The main controller 251 integrally controls the operations of the components of the reinspection apparatus 200.

The input portion 212, the ejector 213, the suction roller 214, and the conveyance path 215 are similar in configuration to the input portion 112, the ejector 113, the suction roller 114, and the conveyance path 115 of the sheet processing apparatus 100, respectively. The input portion 212 receives supplied rejected sheets.

The ejector 213 is provided above the input portion. The ejector 213 comprises the suction roller 214. The suction roller 214 takes in the sheets P set in the input portion 212 one by one into the apparatus. The sheet P taken in by the suction roller 214 is introduced into the conveyance path 215.

The conveyance path 215 conveys the sheet P to each component in the reinspection apparatus 200. The conveyance path 215 comprises a conveyer belt and a driving pulley that are not shown. The conveyance path 215 operates the conveyer belt by an unshown driving motor and the driving pulley. The conveyance path 215 uses the conveyer belt to convey the sheet P taken in by the suction roller 214 at a regular speed. The side of the conveyance path 215 close to the ejector 213 is described as an upstream side, and the side close to the cutter 233 is described as a downstream side.

The conveyance path 215 of the reinspection apparatus 200 conveys the sheet P at a lower speed than the conveyance path 115 of the sheet processing apparatus 100. The conveyance path 215 can inhibit the flapping of the sheet P as compared with the conveyance path 115.

The inspection unit 216 is provided on the conveyance path 215 extending from the ejector 213. The inspection unit 216 comprises image readers, a magnetic detector, and a thickness inspection unit. The inspection unit 216 detects optical characteristic information, mechanical characteristics, and magnetic characteristic information regarding the sheet P. The reinspection apparatus 200 thereby detects the kind (category), fitness level, and authentication of the sheet P.

A pair of image readers are provided to face each other across the conveyance path 215. The image readers read images on both sides of the sheet P conveyed on the conveyance path 215. Each of the pair of image readers comprises a charge coupled device (CCD) camera. The reinspection apparatus 200 retrieves design images on the front and rear sides of the sheet P in accordance with the images obtained by the image readers. The image readers also retrieve images of the identification information printed on the batch card, and send the retrieved images to the main controller 251.

The image readers temporarily store the read images in an unshown memory in the inspection unit 216. The reinspection apparatus 200 can display the images stored in the memory on the operation display 237 in response to an operation input.

The thickness inspection unit inspects the sheet P conveyed on the conveyance path 215 for its thickness. For example, when the detected thickness is equal to or more than a prescribed value, the reinspection apparatus 200 detects the doubly taking of sheets P.

The magnetic detector (magnetic sensor) detects the magnetic characteristic information regarding the sheet P.

The operation display 237 displays various operation guides and processing results to the operator. The operation display 237 may be configured as a touch panel. In this case, the reinspection apparatus 200 detects the various operation inputs from buttons displayed on the operation display 237 and from the operation of the operation display 237 by the operator.

The main controller 251 make various determinations in accordance with the detection results (i.e., the images, magnetism, and thickness detected from the sheet P) by each detector of the inspection unit 216. The main controller 251 determines the category, authentication, and fitness of the sheet P.

The main controller 251 also determines whether to reject the sheet P. The main controller 251 determines, as a rejected sheet, the sheet P which has been determined to be counterfeit, or the sheet P which has been detected to be lying on another sheet by the thickness inspection unit, or the sheet P which cannot be identified.

The main controller 251 determines, as rejected sheets, the sheets P which have caused a short pitch that leads to incorrect detection by each detector because the distance between the front sheet P and the rear sheet P on the conveyance path is short.

The main controller 251 can recognize the identification information on the batch card in accordance with the image of the identification information on the batch card retrieved by the image readers of the inspection unit 216.

The reinspection apparatus 200 conveys, to the accumulators 228 to 231, the sheets P which have been determined to be rejected sheets. The reinspection apparatus 200 also conveys, to the cutter 233, the sheets P which have been determined to be unfit sheets. The cutter 233 comprises a cutting machine 233a and a stacker 233b. The cutting machine 233a of the cutter 233 cuts the conveyed unfit sheet. The cutter 233 accumulates slips of the cut sheets P in the stacker 233b. The stacker 233b comprises an eject port through which the slips can be removed from the outside. That is, the operator can take out the slips of the cut sheets P accumulated in the stacker 233b from the eject port.

The reinspection apparatus 200 conveys, to the rejecter/accumulator 234, the sheets P which have been determined to be rejected sheets. For example, the rejected sheets include doubly-taken sheets that have been abnormally conveyed, defective sheets that are folded or torn, and unidentifiable sheets such as unapproved or counterfeit sheets. The reinspection apparatus 200 also conveys, to the rejecter/accumulator 234, the sheets P and the batch card inserted between the sheets P as rejected sheets.

A plurality of unshown gates are provided on the conveyance path 215 on the downstream side of the inspection unit 216. Each of the gates is controlled by the main controller 251. The main controller 251 controls the operation of each of the gates in accordance with the result of the inspection by the inspection unit 216. Thus, the main controller 251 controls so that the sheet P conveyed on the conveyance path 215 will be conveyed to a predetermined processor.

The main controller 251 also controls each of the gates and the conveyance path so that the rejected sheets which have been determined to be nongenuine or uninspectable sheets which cannot be inspected by the inspection unit 216 are accumulated in the rejecter/accumulator 234. The rejecter/accumulator 234 is configured so that the operator can take out the accumulated sheets P.

The main controller 251 also controls each of the gates and the conveyance path so that the sheets P which have been determined to be fit sheets are conveyed to the accumulators 228 to 231 (collectively referred to as an accumulator 232).

The main controller 251 also controls each of the gates and the conveyance path so that the sheets P which have been determined to be unfit sheets are conveyed to the cutter 233.

The operator can operate the operation display 237 to set any kind (category) of sheet P to be processed by the reinspection apparatus 200.

The main controller 251 associates the counting result of the sheets P conveyed to the accumulator 232 or the cutter 233, the classification of the sheets, the identification information on the batch card, and the determination result with each bundle of the sheets, and stores such information as a reinspection result. The main controller 251 sends the reinspection result to the server 300.

The main controller 251 comprises a memory 251a for previously storing a threshold (second determination threshold) for each item of the inspection by each inspector of the inspection unit 216. The main controller 251 compares a detection value detected by each inspector of the inspection unit 216 with the threshold stored in the memory 251a, and determines by the comparison result the category, authentication, and fitness of the sheet P and also determines whether the sheet P is a rejected sheet.

The second determination threshold stored in the memory 251a may be changed in accordance with the input on the operation display 237.

The server 300 combines the reinspection result sent from the reinspection apparatus 200 with the inspection result sent from the sheet processing apparatus 100, and stores the combined inspection result in the storage medium in the server 300. For example, the server 300 adds the reinspection result to the inspection result which includes identification information corresponding to the identification information included in the reinspection result.

The sheets P discharged as rejected sheets in the sheet processing apparatus 100 account for several percents of the total in general. Therefore, the processing speed required for the reinspection apparatus 200 is lower than that of the sheet processing apparatus 100. Thus, as described above, the reinspection apparatus 200 takes out and conveys the sheets P at a lower speed than the sheet processing apparatus 100. Consequently, the reinspection apparatus 200 can inhibit the flapping of the sheet P during conveyance as compared with the sheet processing apparatus 100.

Each of the detectors of the inspection unit 116 and the inspection unit 216 detects each value by the timing (timing clock) synchronized with the conveyance speed of the sheets P. In this case as well, the reinspection apparatus 200 conveys the sheet P at a lower speed than the sheet processing apparatus 100, so that each of the detectors of the inspection unit 216 can detect each value in more detail as compared with the inspection unit 116. That is, each of the detectors of the inspection unit 216 can detect each value in a shorter sampling period than the inspection unit 116.

The reinspection apparatus 200 can inspect the sheet P for its characteristics in more detail as compared with the sheet processing apparatus 100 on the basis of the accurate data detected as described above. As a result, the reinspection apparatus 200 can more accurately determine the rejected sheets which have been determined to be unidentifiable by the sheet processing apparatus 100.

The reinspection apparatus 200 can use a longer time to determine one sheet P than the sheet processing apparatus 100. Therefore, the reinspection apparatus 200 can use a more complicated calculation to determine the sheet P than the sheet processing apparatus 100. For example, the reinspection apparatus 200 can use more inspection items to determine the sheet P than the sheet processing apparatus 100.

For example, the sheet processing apparatus 100 uses a part of the top of the sheet P to determine the sheet P. In contrast, the reinspection apparatus 200 can use more parts of the top of the sheet P to determine the sheet P than the sheet processing apparatus 100.

As a result, the reinspection apparatus 200 can use the inspection items different from those used by the sheet processing apparatus 100 to determine various characteristics of the sheet P. Thus, the reinspection apparatus 200 can accurately determine the characteristics of the sheet P as compared with the sheet processing apparatus 100.

As the reinspection apparatus 200 conveys the sheet P at a lower speed than the sheet processing apparatus 100, each detector of the inspection unit 216 can detect each value with less variation of the sheets P as compared with the inspection unit 116. Therefore, the reinspection apparatus 200 can set a wider acceptance range of the second determination threshold stored in the memory 251a than that of the first determination threshold stored in the memory 151a of the sheet processing apparatus 100.

Figure 7:
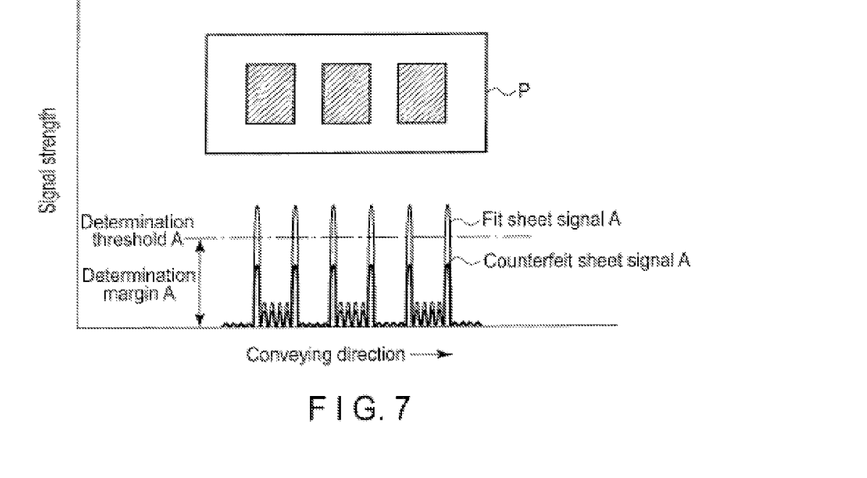
FIG. 7 is an exemplary view for explaining the sheet reinspection apparatus according to the embodiment.

FIG. 7 shows an example of a detection result and the determination threshold when the sheet P remains stationary.

When the sheet P remains stationary, the sheet P does not flap. Therefore, detection values detected from the sheets P by the inspector do not vary by the sheets P. As a result, there is a great difference between the detection value (fit sheet signal A) detected from the fit sheet P and the detection value (counterfeit sheet signal A) detected from the counterfeit sheet P.

Figure 8:
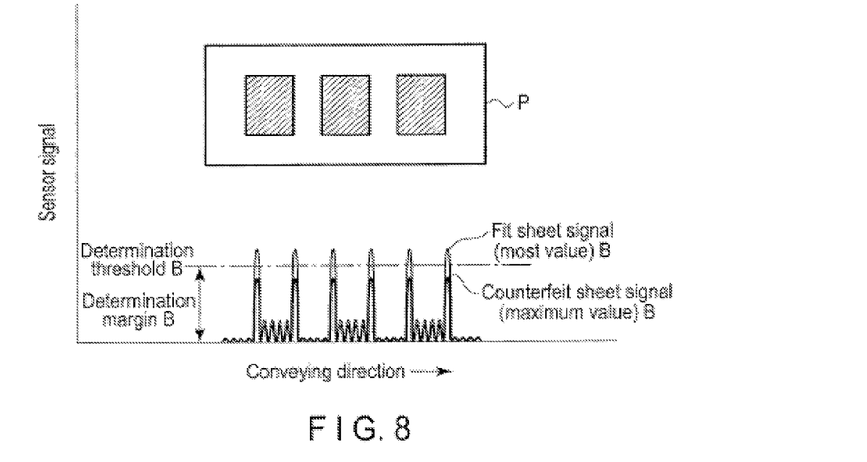
FIG. 8 is an exemplary view for explaining the sheet reinspection apparatus according to the embodiment.

FIG. 8 shows an example of a detection result of the sheet P by the sheet processing apparatus 100 and the first determination threshold set in the memory 151a.

The sheet processing apparatus 100 processes the sheets P at a higher speed than the reinspection apparatus 200. Therefore, detection values detected from the sheets P by the inspectors of the inspection unit 116 vary by the sheets P. Thus, there may be a smaller difference between the detection value (fit sheet signal B) detected from the fit sheet P and the detection value (counterfeit sheet signal B) detected from the counterfeit sheet P.

Figure 9:
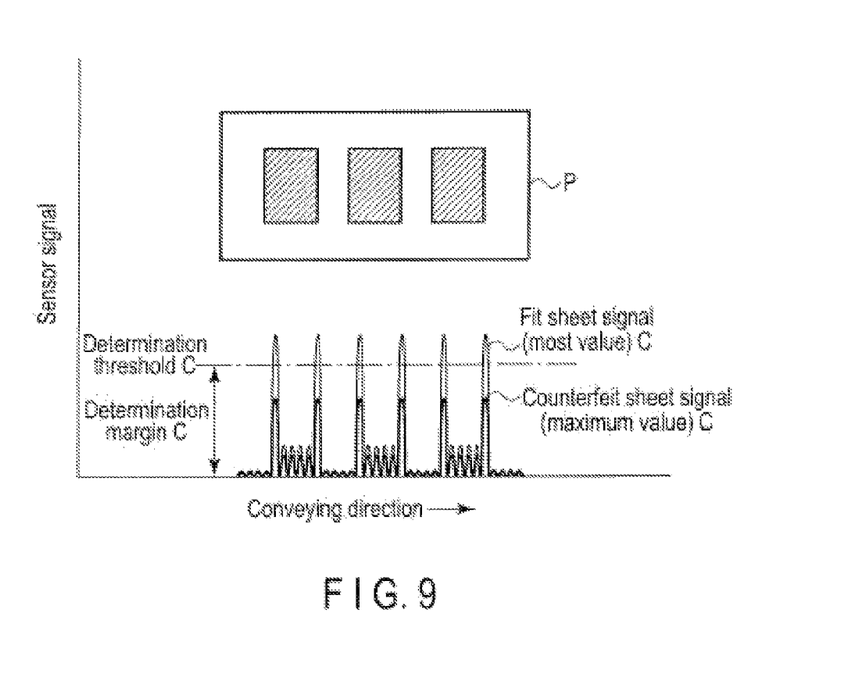
FIG. 9 is an exemplary view for explaining the sheet reinspection apparatus according to the embodiment.

FIG. 9 shows an example of a detection result of the sheet P by the reinspection apparatus 200 and the second determination threshold set in the memory 251a.

The reinspection apparatus 200 processes the sheets P at a lower speed than the sheet processing apparatus 100. Therefore, detection values detected from the sheets P by the inspectors of the inspection unit 216 vary less than in the sheet processing apparatus 100. Thus, there is a greater difference between the detection value (fit sheet signal C) detected from the fit sheet P and the detection value (counterfeit sheet signal C) detected from the counterfeit sheet P than in the detection result by the sheet processing apparatus 100.

That is, the fit sheet signals (most values) A, B, and C satisfy the relation "fit sheet signal A>fit sheet signal B>fit sheet signal C". The counterfeit sheet signals (maximum values) A, B, and C satisfy the relation "counterfeit sheet signal A=counterfeit sheet signal B=counterfeit sheet signal C". As a result, determination margins satisfy the relation "determination margin C>determination margin B". That is, the possibility of the rejection of the same fit sheet P by the reinspection apparatus 200 is compared with the possibility of the rejection by the sheet processing apparatus 100. The sheet processing apparatus 100 needs to have a narrower acceptance range indicated by the first determination threshold in order to prevent the counterfeit sheet from being determined to be a fit sheet. Therefore, the sheet processing apparatus 100 has the first determination threshold B (with a narrower acceptance range) set therein such that the same sheet P is more easily determined to be a rejected sheet than in the reinspection apparatus 200. The reinspection apparatus 200 is less likely to determine a counterfeit sheet to be a fit sheet than the sheet processing apparatus 100 because the sheets P flap less. Therefore, the reinspection apparatus 200 has the second determination threshold C (with a wide acceptance range) set therein such that the same sheet P is less easily determined to be a rejected sheet as compared with the sheet processing apparatus 100.

That is, the reinspection apparatus 200 can set, as the second determination threshold, a threshold by which the sheet P is more easily determined to be a genuine sheet than by the first determination threshold. As a result, it is possible to provide a sheet reinspection apparatus, a sheet inspection system, and a sheet inspection method that enable more efficient sheet inspection.

The reinspection apparatus 200 conducts a reinspection in the normal processing mode in a normal state (default state). The normal processing mode is a prescribed processing mode for the reinspection of rejected sheets. When operating in the normal processing mode, the reinspection apparatus 200 conducts the reinspection described above. Moreover, when operating in the normal processing mode, the reinspection apparatus 200 saves the number of sheets P which have been determined to be fit sheets or unfit sheets, and the number of determination results for the respective inspection items.

Furthermore, the reinspection apparatus 200 conducts the reinspection in the check processing mode for the sheets P which have been rejected in the normal processing mode. The check processing mode is a mode for the operator who operates the reinspection apparatus 200 to invalidate the sheets P which have been determined to be effective (fit or unfit) by a visual check. The reinspection apparatus 200 is switched from the normal mode to the check processing mode in accordance with the operation input on the operation display 237. The reinspection apparatus 200 may be configured to be automatically switched from the normal processing mode to the check processing mode when rejected sheets are generated in the normal processing mode.

When operating in the check processing mode, the reinspection apparatus 200 can inspect the sheets with items fewer than the items used for the determination of the sheets than in the normal processing mode. Thus, when operating in the check processing mode, the reinspection apparatus 200 can exclude, from inspection items, items which can be visually checked by the operator. That is, when operating in the check processing mode, the reinspection apparatus 200 reinspects the sheets P with a second inspection item set having fewer inspection items than an inspection item set (first inspection item set) of the normal processing mode. Moreover, the reinspection apparatus 200 cuts the counted sheets P with the cutter 233.

The reinspection apparatus 200 may be configured to change the determination threshold of a particular inspection item instead of excluding a particular item from the inspection items. For example, when operating in the check processing mode, the reinspection apparatus 200 changes the determination threshold of the items which can be visually checked by the operator to a value (with a wide acceptance range) by which the sheet P is less easily determined to be a rejected sheet than in the normal processing mode. Consequently, the reinspection apparatus 200 can prevent the increase of the number of sheet reinspections.

The items which can be visually checked by the operator are, for example, watermarks, tape bonding, and the degree of a defect. When operating in the check processing mode, the reinspection apparatus 200 excludes these items from the inspection items or changes the determination threshold used for the inspection of these items.

The reinspection apparatus 200 is switched from the check processing mode to a non-inspection counting mode in accordance with the operation input on the operation display 237. The reinspection apparatus 200 may be configured to be automatically switched from the check processing mode to the non-inspection counting mode when a rejected sheet is generated in the check processing mode. Moreover, the reinspection apparatus 200 may be configured to permit the switch to the non-inspection counting mode when predetermined authentication processing that uses a password is performed.

When operating in the non-inspection counting mode, the reinspection apparatus 200 counts the number of sheets without determining the category, authentication, and fitness level of the sheet. That is, the reinspection apparatus 200 can count the number of sheets which have been ascertained to be fit sheets by the operator, without determination. As a result, the reinspection apparatus 200 can prevent the increase of the number of sheet reinspections. When operating in the non-inspection counting mode, the reinspection apparatus 200 cuts the counted sheets P with the cutter 233.

When operating in the non-inspection counting mode, the reinspection apparatus 200 retrieves images from the sheets. The reinspection apparatus 200 also retrieves a detection value by each inspection unit. When operating in the non-inspection counting mode, the reinspection apparatus 200 stores, as a processing history, the images of the sheets, the detection value by each inspection unit, the date of processing, the operator's name, the classification of the sheets, the identification information on the batch card, and other information in association with one another.

The reinspection apparatus 200 can display each piece of information regarding the processing history on the operation display 137 in response to an operation input. In response to an operation input, the reinspection apparatus 200 can display, on the operation display 137, the stored images of the sheets P, the detection value by each inspection unit, the date of processing, the operator's name, the classification of the sheets, the identification information on the batch card, and other information. Moreover, in response to an operation input, the reinspection apparatus 200 can specify one or more of the conditions including the stored images of the sheets P, the detection value by each inspection unit, the date of processing, the operator's name, the classification of the sheets, the identification information on the batch card, and other information. The reinspection apparatus 200 can then display, on the operation display 137, the inspection result (the detection value by each inspection unit) corresponding to the specified condition.

As a result of one of the three kinds of processing modes described above, all the rejected sheets are counted and invalidated. In this case, the reinspection apparatus 200 sends the counting result, that is, the reinspection result to the server 300.

The server 300 combines the reinspection result sent from the reinspection apparatus 200 with the inspection result sent from the sheet processing apparatus 100, and stores the combined inspection result in the storage medium in the server 300. For example, the server 300 adds the reinspection result to the inspection result which includes identification information corresponding to the identification information included in the reinspection result. In this way, the server 300 calculates the sum of the number of the sheets P which have been determined to be fit sheets by the sheet processing apparatus 100 or the reinspection apparatus 200, and the number of the sheets P which have been determined to be unfit sheets. When the additional result by the server 300 corresponds to a previously input expected number, a series of inspections of the sheets P is completed by the operator.

As described above, the reinspection apparatus 200 can make determinations by using such a threshold that the sheets are more easily determined to be recirculatable fit sheets. As a result, the reinspection apparatus 200 can prevent the increase of the number of sheet reinspections. The reinspection apparatus 200 stores, in a traceable manner, the detection value by the inspection unit 216 that has been used for the inspection. Thus, the reinspection apparatus 200 can prevent improper counting of the sheets P. As a result, it is possible to provide a sheet reinspection apparatus, a sheet inspection system, and a sheet inspection method that enable more efficient sheet inspection with higher security.

Functions described in the above embodiment may be constituted not only with use of hardware but also with use of software, for example, by making a computer read a program which describes the functions. Alternatively, the functions each may be constituted by appropriately selecting either software or hardware.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A reinspection apparatus which reinspects rejected sheets rejected from a sheet processing apparatus configured to convey sheets at a first speed, to inspect the conveyed sheet in accordance with a first determination threshold, and to reject the sheets in accordance with an inspection result, the reinspection apparatus comprising:
- a taking unit configured to take in, one by one, the sheets as the rejected sheets rejected from the sheet processing apparatus;
- a conveying unit configured to convey the taken sheets at a second speed lower than the first speed;
- an inspection unit configured to inspect the sheets conveyed at the second speed;
- a determination unit configured to determine whether to reject the sheets in accordance with the result of the inspection;
- a counting unit configured to count the sheets which have been determined not to be rejected in accordance with the result of the determination; and
- an output unit configured to output the result of the counting,
- wherein the determination unit comprises a memory configured to store a second determination threshold having a wider acceptance range than the first determination threshold,
- the inspection unit retrieves a detection value from the sheets conveyed at the second speed, and
- the determination unit determines whether to reject the sheets in accordance with the second determination threshold and the detection value.

2. The reinspection apparatus according to claim 1, wherein the inspection unit retrieves a detection value from the sheets in a smaller period than the sheet processing apparatus.

3. The reinspection apparatus according to claim 1, wherein the inspection unit retrieves detection values of more items from the sheets than the sheet processing apparatus.

4. A sheet inspection system comprising a sheet processing apparatus and a reinspection apparatus which reinspects rejected sheets rejected from the sheet processing apparatus, wherein
the sheet processing apparatus comprises
- a first taking unit configured to take in the sheets one by one,
- a first conveying unit configured to convey the taken sheets at a first speed,
- a first inspection unit configured to inspect the sheets conveyed at the first speed,
- a first determination unit configured to determine whether to reject the sheets in accordance with the result of the inspection,
- a first counting unit configured to count the sheets which have been determined not to be rejected in accordance with the result of the determination, and
- a first output unit configured to output the result of the counting, and the reinspection apparatus comprises
- a second taking unit configured to take in, one by one, the sheets as the rejected sheets which have been determined by the first determination unit to be rejected,
- a second conveying unit configured to convey the taken sheets at a second speed lower than the first speed,
- a second inspection unit configured to inspect the sheets conveyed at the second speed,
- a second determination unit configured to determine whether to reject the sheets in accordance with the result of the inspection,
- a second counting unit configured to count the sheets which have been determined not to be rejected in accordance with the result of the determination, and
- a second output unit configured to output the result of the counting.

5. A sheet inspection method for use in a sheet inspection system comprising:
- taking in the sheets one by one by a sheet processing apparatus,
- conveying the taken sheets at a first speed by the sheet processing apparatus,
- inspecting the sheets conveyed at the first speed by the sheet processing apparatus,
- determining whether to reject the sheets in accordance with the result of the inspection by the sheet processing apparatus,
- counting the sheets which have been determined not to be rejected in accordance with the result of the determination by the sheet processing apparatus, and
- outputting the result of the counting by the sheet processing apparatus; and
- taking in, one by one, the sheets as the rejected sheets which have been determined to be rejected by the sheet processing apparatus by a reinspection apparatus,
- conveying the taken sheets at a second speed lower than the first speed by the reinspection apparatus,
- inspecting the sheets conveyed at the second speed by the reinspection apparatus,
- determining whether to reject the sheets in accordance with the result of the inspection by the reinspection apparatus,
- counting the sheets which have been determined not to be rejected in accordance with the result of the determination by the reinspection apparatus, and
- outputting the result of the counting by the reinspection apparatus.

\* \* \* \* \*